United States Patent [19]

Saüter et al.

[11] Patent Number: 4,575,504

[45] Date of Patent: Mar. 11, 1986

[54] THIENOTHIAZOLE DERIVATIVES

[75] Inventors: Robert Saüter, Biberach; Gerhart Griss, deceased, late of Biberach, by Elisabeth Griss, executrix; Wolfgang Grell; Rudolf Hurnaus, both of Biberach, all of Fed. Rep. of Germany; Walter Kobinger; Ludwig Pichler, both of Vienna, Austria

[73] Assignee: Dr. Karl Thomae GmbH, Biberach an der Riss, Fed. Rep. of Germany

[21] Appl. No.: 649,898

[22] Filed: Sep. 12, 1984

Related U.S. Application Data

[63] Continuation-in-part of Ser. No. 520,163, Aug. 4, 1983, abandoned.

[30] Foreign Application Priority Data

Aug. 18, 1982 [DE] Fed. Rep. of Germany ....... 3230696

[51] Int. Cl.[4] .................... A61K 31/44; A61K 31/55; C07D 513/14
[52] U.S. Cl. ................. 514/215; 260/245.5; 260/239 B; 260/239 BF; 260/330.3; 514/293; 546/83; 546/114
[58] Field of Search ...................... 260/245.5; 546/83; 514/215, 293

[56] References Cited

U.S. PATENT DOCUMENTS

| | | | |
|---|---|---|---|
| 3,882,125 | 5/1975 | Dohmori et al. | 546/83 |
| 4,220,776 | 9/1980 | Whitney et al. | 546/83 |
| 4,244,952 | 1/1981 | Munakata et al. | 546/83 |
| 4,275,065 | 6/1981 | Wei et al. | 546/83 |
| 4,414,225 | 11/1983 | Sauter et al. | 514/215 |

FOREIGN PATENT DOCUMENTS 2722416  11/1978  Fed. Rep. of Germany ...... 514/215

OTHER PUBLICATIONS

Taurins et al., Can. J. Chem., vol. 49, pp. 4054–4064 (1971).

*Primary Examiner*—Alton D. Rollins
*Attorney, Agent, or Firm*—Hammond & Littell, Weissenberger & Dippert

[57] ABSTRACT

Compounds of the formula

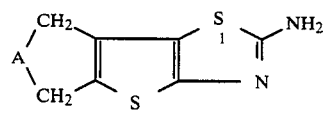

wherein
A is

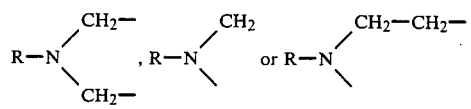

and
R is hydrogen, alkyl of 1 to 5 carbon atoms, alkanoyl of 1 to 5 carbon atoms, alkenyl of 3 to 5 carbon atoms, (alkoxy of 1 to 4 carbon atoms)carbonyl, or aralkyl of 7 to 11 carbon atoms optionally halo-substituted, and non-toxic, pharmacologically acceptable acid addition salts thereof. The compounds as well as their salts are useful as bradycardiacs.

8 Claims, No Drawings

THIENOTHIAZOLE DERIVATIVES

This is a continuation-in-part application of co-pending application Ser. No. 520,163, filed Aug. 4, 1983, now abandoned.

This invention relates to novel thienothiazole derivatives and non-toxic acid addition salts thereof, to methods of preparing these compounds, to pharmaceutical compositions containing them as active ingredients, and to a method of using them as bradycardiacs.

More particularly, the present invention relates to a novel class of compounds represented by the formula

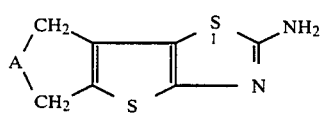

wherein
A is

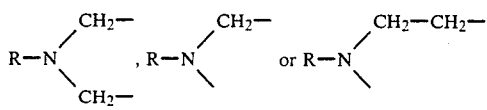

and

R is hydrogen, alkyl of 1 to 5 carbon atoms, alkanoyl of 1 to 5 carbon atoms, alkenyl of 3 to 5 carbon atoms, (alkoxy of 1 to 4 carbon atoms)carbonyl, or aralkyl of 7 to 11 carbon atoms optionally halo-substituted;

and non-toxic, pharmacologically acceptable acid addition salts thereof.

Thus the present invention relates to N-substituted derivatives of 2-amino-6,7,8,9-tetrahydro-5H-thiazolo[4',5':5,4]thieno[2,3-d]azepine, 2-amino-5,6,7,8-tetrahydro-thiazolo[4',5':5,4]thieno[3,2-c]pyridine, 2-amino-5,6,7,8-tetrahydro-thiazolo[4',5':5,4]thieno[2,3-c]pyridine, 2-amino-6,7,8,9-tetrahydro-5H-thiazolo[4',5':5,4]thieno[2,3-c]azepine and 2-amino-6,7,8,9-tetrahydro-5H-thiazolo[4',5':5,4]thieno[3,2-c]azepine.

Specific examples of substituents represented by R in formula I are the following: Hydrogen, methyl, ethyl, n-propyl, isopropyl, n-butyl, isobutyl, tert.butyl, n-pentyl, neopentyl, tert. pentyl, formyl, acetyl, propionyl, n-butanoyl, n-pentanoyl, 2-methylpropionyl, pivaloyl, allyl, crotyl, penten-2-yl, penten-3-yl, methoxycarbonyl, ethoxycarbonyl, n-propoxycarbonyl, isopropoxycarbonyl, n-butoxycarbonyl, isobutoxycarbonyl, tert. butoxycarbonyl, benzyl, 1-phenylethyl, 2-phenylethyl, 3-phenylpropyl, naphthylmethyl, chlorobenzyl, bromobenzyl, fluorobenzyl, 1-chlorophenylethyl, 2-bromophenylethyl or 3-chlorophenyl-propyl.

A preferred subgenus is constituted by those 2-amino-6,7,8,9-tetrahydro-5H-thiazolo[4',5':5,4]thieno[2,3-d]azepine, 2-amino-5,6,7,8-tetrahydro-thiazolo[4',5':5,4]thieno[3,2-c]pyridine, 2-amino-5,6,7,8-tetrahydro-thiazolo[4',5':5,4]thieno[2,3-c]pyridine and 2-amino-6,7,8,9-tetrahydro-5H-thiazolo[4',5':5,4]thieno[2,3-c]azepine derivatives of the formula I
wherein
R is hydrogen, alkyl of 1 to 4 carbon atoms, alkanoyl of 1 to 3 carbon atoms, (alkoxy of 1 to 3 carbon atoms)carbonyl, benzyl, chlorobenzyl, bromobenzyl or allyl, and non-toxic, pharmacologically acceptable acid addition salts thereof.

A particularly preferred subgenus is constituted by those 2-amino-6,7,8,9-tetrahydro-5H-thiazolo[4',5':5,4]thieno[2,3-c]azepine and 2-amino-5,6,7,8-tetrahydro-thiazolo[4',5':5,4]thieno[2,3-c]pyridine derivatives of the formula I
wherein
R is hydrogen, alkyl of 1 to 3 carbon atoms, allyl or benzyl, and non-toxic, pharmacologically acceptable acid addition salts thereof.

The compounds embraced by formula I may be prepared by the following methods:

Method A

By reacting a thiophene of the formula

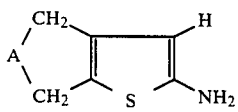

wherein A has the meanings previously defined, with dithiocyanogen.

The thiophene as well as the dithiocyanogen may optionally be prepared in situ in the reaction mixture.

The reaction is preferably carried out in a solvent or mixture of solvents, such as glacial acetic acid, acetic acid/water, dioxane/acetic acid, methanol, tetrahydrofuran or dilute hydrochloric acid, at temperatures between $-5°$ and $50°$ C., preferably between $0°$ and $25°$ C.

The dithiocyanogen required for the reaction is conveniently prepared by oxidation of thiocyanic acid, for example with chlorine, bromine or a heavy metal salt such as copper sulfate, or by anodic oxidation, the thiocyanic acid in turn being liberated from a salt of thiocyanic acid, preferably an alkali metal salt such as the sodium or potassium salt, by means of an acid such as acetic, hydrochloric or sulfuric acid, or by decomposition of a corresponding heavy metal salt such as copper dithiocyanate.

Furthermore, a compound of the formula II may be prepared in the reaction mixture by decarboxylating a corresponding 2-amino-3-carboxy compound, or by hydrolysis and subsequent decarboxylation of a corresponding alkoxycarbonylamino compound in the presence of an acid such as trifluoroacetic acid, glacial acetic acid/hydrobromic acid or dioxane/hydrochloric acid.

Method B

For the preparation of a compound of the formula I wherein R is methyl optionally substituted by alkyl of 1 to 4 carbon atoms:

By reducing a compound of the formula

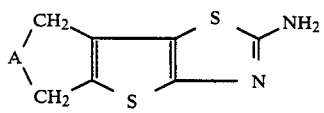

wherein A is

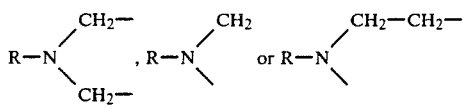

wherein R₁ is alkanoyl of 1 to 5 carbon atoms or a carbonic acid ester group such as ethoxycarbonyl, phenoxycarbonyl or benzyloxycarbonyl.

The reduction is carried out in the presence of an hydride and conveniently in a suitable solvent such as diethyl ether, tetrahydrofuran, dioxane or pyridine/tetrahydrofuran at temperatures between 0° and 100° C., preferably at the boiling point of the solvent which is used. The reduction is preferably effected with lithium aluminum hydride, sodium aluminum hydride, lithium borohydride, a sodium acyloxy borohydride such as sodium acetoxy borohydride or pyridine/borane.

The compounds embraced by formula I are basic substances and therefore form addition salts with inorganic or organic acids. Examples of non-toxic, pharmacologically acceptable acid addition salts are those formed with hydrochloric, hydrobromic, sulfuric, phosphoric, lactic, citric, tartaric, maleic or fumaric acid.

The starting compounds of the formulas II and III, which may be used as crude products, may be obtained by processes described in the literature, for instance by Vilsmeier reaction of a corresponding cyclic ketone, converting the chloroformyl compound thus obtained into the corresponding nitrile via the oxime, reacting the resulting nitrile with a thioglycol ester and subsequently cyclizing the reaction product. The esters thus obtained may subsequently be decarboxylated after hydrolysis. Some of the compounds of the formulas II and III are described in published European Application No. 0,058,341, or may be prepared by the processes described therein.

The following examples illustrate the present invention and will enable others skilled in the art to understand it more completely. It should be understood, however, that the invention is not limited solely to the particular examples given below.

Preparation of starting compounds:

EXAMPLE A

Diethyl 2-amino-5,6,7,8-tetrahydro-4H-thieno[2,3-c]azepine-3,7-dicarboxylate 3.7 g (0.02 mol) of ethyl hexahydro-azepinone-(4)-1-carboxylate together with 2.26 g (0.02 mol) of ethyl cyanoacetate and 0.65 g (0.02 mol) of sulfur were suspended in 20 ml of ethyl alcohol. 5 ml of morpholine were added dropwise to this suspension while stirring, whereupon the temperature rose to about 30° C. The mixture was stirred for three hours at 50° C. and was then allowed to stand overnight at room temperature. The next day, the solid product which had precipitated was suction-filtered off and recrystallized from isopropyl alcohol.

Yield: 3.6 g (58% of theory).

M.p.: 104°–106° C.

Calculated: C-53.86%; H-6.41%; N-8.98%; S-10.25%, Found: C-53.90%; H-6.40%; N-9.04%; S-10.32%.

EXAMPLE B

Methyl 2-amino-5,6,7,8-tetrahydro-4H-thieno[2,3-d]azepine-3-carboxylate hydrochloride A solution of 11.1 g (0.15 mol) of sodium hydrogen sulfide in 120 ml of methyl alcohol was added dropwise, over a period of 25 minutes, at 10° to 15° C., to a solution of 41 g (0.15 mol) of 5-bromo-hexahydro-azepinone-(4)-hydrobromide in 90 ml of methyl alcohol. After the mixture had been stirred for 20 minutes at 10° to 15° C., 14.9 g (0.15 mol) of methyl cyanoacetate were added thereto. Then 21.9 g (0.3 mol) of diethylamine were added dropwise over a period of 20 minutes, while vigorously stirring, whereupon the internal temperature rose from 8° to 26° C. The mixture was then stirred for two hours at 40° C. After cooling, it was evaporated in vacuo, the residue was taken up in dilute sodium hydroxide and extracted with chloroform. The chloroform phases were washed with dilute sodium hydroxide and water, dried over sodium sulfate and concentrated by evaporation in vacuo. The residue was chromatographed on a silicagel column (chloroform/methanol/aqueous ammonia=7:4:0.25). After the corresponding fractions had been combined, they were evaporated in vacuo. The residue was taken up in methanol, and the hydrochloride was precipitated with isopropanolic hydrochloric acid and then suction-filtered off. The sparsely soluble salt was briefly boiled twice with methanol.

Yield: 5.4 g (13.7% of theory).

M.p.: from 256° C. (decomposition).

Calculated: C-45.71%; H-5.75%; N-10.66%; Cl-13.49%; S-12.20%, Found: C-45.67%; H-5.81%; N-10.64%; Cl-13.50%; S-12.04%.

EXAMPLE C 2-(N-tert.butoxycarbonylamino)-6-propyl-5,6,7,8-tetrahydro-4H-thieno[2,3-d]azepine 8.5 g (0.0335 mol) of 5,6,7,8-tetrahydro-6-propyl-4H-thieno[2,3-d]azepine-2-carboxylic acid hydrazide were dissolved in 70 ml of 2N hydrochloric acid and diazotized with a solution of 2.8 g (0.04 mol) of sodium nitrite in 10 ml of water at −5° to 0° C. The mixture was stirred for 50 minutes at 0° C., and the thick crystal slurry formed thereby was separated into layers with 150 ml of methylene chloride. Then, 40 ml of concentrated ammonia solution were added dropwise, the methylene chloride phase was separated, and the aqueous phase was extracted several times with methylene chloride. The combined methylene chloride phases were dried over sodium sulfated and concentrated by evaporation in a rotary evaporator at a bath temperature of 30° C. Then, the evaporation residue was mixed twice with benzene and evaporated in vacuo.

Yield of azide: 8.5 g (95.8% of theory), light-brown oil.

The substance (0.032 mol) was dissolved in 25 ml of absolute dioxane, and the solution was added dropwise over a period of 30 minutes to a mixture of 30 ml of absolute dioxane and 2.9 g (0.0385 mol) of tert.butyl alcohol which has been heated to 90° C., whereupon a vigorous evolution of nitrogen occurred. The mixture was then heated at its boiling point for 1.5 hours and then allowed to cool overnight. The next day, it was concentrated by evaporation in vacuo, and the residue was chromatographed on a silicagel column (ethyl acetate/ethyl alcohol/concentrated aqueous ammonia=0.2:7:0.7). After the corresponding fractions had been combined, they were concentrated by evaporation in vacuo.

Yield: 5.5 g (55% of theory).
M.p. 141°–143° C.

EXAMPLE D

6-Ethyl-2-amino-5,6,7,8-tetrahydro-4H-thieno[2,3-d]azepine dihydrobromide 2.0 g (0.0068 mol) of 6-ethyl-2-(N-tert.butoxycarbonylamino)-5,6,7,8-tetrahydro-4H-thieno[2,3-d]azepine were added to 18 ml of a 40% glacial acetic acid/hydrobromic acid solution while dry nitrogen was introduced, accompanied by stirring and cooling to 0° C. After 3 hours' stirring at 0° C., 60 ml of absolute ether were added dropwise thereto, and the resulting mixture was stirred for 15 minutes and then decanted. After absolute ether had been added and the mixture had been decanted several times, the initially tacky substance became crystalline and capable of being suction-filtered. It was washed several times with absolute ether and dried in a desiccator over phosphorous pentoxide.

Yield: 1.8 g (75% of theory).
M.p.: from 50° C. (decomposition).
Calculated: C-33.54%; H-5.07%; N-7.82%; Br-44.62%; S-8.95%, Found: C-33.80%; H-5.29%; N-7.36%; Br-44.30%; S-8.84%.

The following compounds were prepared in analogy to Examples A to D:

(1) Ethyl 2-amino-6-benzyl-5,6,7,8-tetrahydro-4H-thieno[2,3-d]azepine-3-carboxylate hydrochloride
Yield: 23% of theory.
M.p.: 228°–229° C. (decomposition).
Calc.: C-58.93%; H-6.32%; N-7.63%; Cl-9.66%; S-8.74%, Found: C-58.64%; H-6.32%; N-7.36%; Cl-9.34%; S-8.52%.

(2) Ethyl 6-ethyl-2-amino-5,6,7,8-tetrahydro-4H-thieno[2,3-d]azepine-3-carboxylate oxalate
Yield: 32% of theory.
M.p. 173°–174° C. (decomposition).
Calc.: C-50.27%; H-6.19%; N-7.82%; S-8.94%, Found: C-50.25%; H-6.36%; N-7.64%; S-9.23%.

(3) Ethyl 6-allyl-2-amino-5,6,7,8-tetrahydro-4H-thieno[2,3-d]azepine-3-carboxylate
Yield: 26.1% of theory, red oil.
Calculated: molecular ion peak m/e=280, Found: molecular ion peak m/e=280.

(4) Diethyl 2-amino-5,6,7,8-tetrahydro-4H-thieno[2,3-d]azepine-3,6-dicarboxylate and Diethyl 2-amino-5,6,7,8-tetrahydro-4H-thieno[2,3-c]azepine-3,7-dicarboxylate
Yield: 16.1% of theory.
M.p. 122°–125° C.
Calculated: C-53.83%; H-6.45%; N-8.97%; S-10.26%, Found: C-54.00%; H-6.35%; N-9.16%; S-10.06%.

(5) 2-(N-tert.butoxycarbonylamino)-5,6,7,8-tetrahydro-6-isopropyl-4H-thieno[2,3-d]azepine
Yield: 38.5% of theory.
Calculated: C-61.90%; H-8.44%; N-9.02%; S-10.33%, Found: C-61.68%; H-8.56%; N-9.18%; S-10.19%.

(6) 2-Amino-5,6,7,8-tetrahydro-6-isopropyl-4H-thieno[2,3-d]azepine dihydrobromide
Yield: 83.5% of theory.

Calc.: C-35.50%, H-5.42%; N-7.53%; S-8.61%; Br-42.94%, Found: C-35.19%, H-5.63%; N-7.64%; S-8.32%; Br-42.51%.

(7) 6-Allyl-2-(N-tert.butoxycarbonylamino)-5,6,7,8-tetrahydro-4H-thieno[2,3-d]azepine
Yield: 29.6% of theory.
M.p.: 135°–137° C.
Calc.: C-62.31%; H-7.84%; N-9.08%; S-10.39%, Found: C-62.40%; H-7.93%; N-9.06%; S-10.50%.

(8) 6-Allyl-2-amino-5,6,7,8-tetrahydro-4H-thieno[2,3-d]azepine dihydrobromide
Yield: 83.3% of theory.
M.p.: from 50° C. (decomposition).
Calc.: C-35.69%; H-4.90%; N-7.57%; Br-43.18%; S-8.66%, Found: C-35.70%; H-5.33%; N-6.95%; Br-42.70%; S-8.36%.

(9) 2-Amino-6-(4-chloro-benzyl)-5,6,7,8-tetrahydro-4H-thieno[2,3-d]azepine dihydrobromide
Yield: 75% of theory.
M.p.: from 225° C. (decomposition).
Calculated: molecular ion peak m/e=292/294 (1 Cl), Found: molecular ion peak m/e=292/294 (1 Cl).

(10) 6-Benzyl-2-(N-tert.butoxycarbonylamino)-5,6,7,8-tetrahydro-4H-thieno[2,3-d]azepine
Yield: 45% of theory, yellow oil.
Calculated: molecular ion peak m/e=358; Found: molecular ion peak m/e=358.

(11) 2-Amino-6-benzyl-5,6,7,8-tetrahydro-4H-thieno[2,3-d]azepine dihydrobromide
Yield: 84% of theory.
M.p.: 232°–234° C.
Calc.: C-42.87%; H-4.80%; N-6.67%; Br-38.03%; S-7.63%, Found: C-42.90%; H-4.87%; N-6.37%; Br-37.90%; S-7.80%.

(12) 6-Ethyl-2-(N-tert.butoxycarbonylamino)-5,6,7,8-tetrahydro-4H-thieno[2,3-d]azepine
Yield: 30.5% of theory.
M.p.: 149°–151° C.
Calc.: C-60.78%; H-8.16%; N-9.45%; S-10.82%, Found: C-61.00%; H-8.22%; N-9.40%; S-11.04%.

(13) 5-Ethyl-2-(N-tert.butoxycarbonylamino)-5,6,7,8-tetrahydro-4H-thieno[3,2-c]azepine
Yield: 67.5% of theory.
M.p.: 154°–156° C.

(14) 5-Ethyl-2-amino-5,6,7,8-tetrahydro-4H-thieno[3,2-c]azepine dihydrobromide
Yield: 100% of theory (hygroscopic).
M.p.: sintering from 100° C.; from 210° C. (decomposition).

Preparation of end products of the formula I:

EXAMPLE 1

7-Ethyl-2-amino-6,7,8,9-tetrahydro-5H-thiazolo[4',5':5,4]thieno[2,3-d]azepine dihydrochloride 16.9 g (0.063 mol) of 6-ethyl-2-amino-5,6,7,8-tetrahydro-4H-thieno[2,3-d]azepine dihydrochloride were stirred in 200 ml of glacial acetic acid, with the addition of 10 ml of water, until completely dissolved. Then, a solution of 36.6 g (0.37 mol) of potassium thiocyanate in 40 ml of water was added, and a solution of 10.0 g of bromine (0.063 mol) in 30 ml of glacial acetic acid was slowly added dropwise thereto. After the reaction had subsided, the mixture was stirred for one hour and then allowed to stand overnight. After the insoluble matter had been filtered off, the residue was concentrated by evaporation in vacuo, the black evaporation residue was digested several times with warm water and suction-filtered each time through diatomaceous earth. The combined aqueous filrates were made alkaline with concentrated ammonia, then cooled in ice water, the precipitated solid product was suction-filtered and washed twice with cold water. After drying, the substance was stirred for 3 hours in chloroform at room temperature, then suction-filtered, washed with cold chloroform and dried.

The light brown crystals were dissolved in hot methanol, with the addition of some chloroform, and acidified with ethanolic hydrochloric acid. After cooling in ice water, the dihydrochloride was suction-filtered off and dried.

Yield: 6 g (30% of theory).
M.p.: 256° C. (decomposition).
Calculated: C-40.49%; H-5.25%; Cl-21.73%; N-12.88%; S-19.65%, Found: C-40.60; H-5.12%; Cl-21.55%; N-13.01%; S-19.50%.

EXAMPLE 2

2-Amino-7-benzyl-6,7,8,9-tetrahydro-5H-thiazolo[4',5':5,4]thieno[2,3-d]azepine

This compound was prepared from 2-amino-6-benzyl-5,6,7,8-tetrahydro-4H-thieno[2,3-d]azepine dihydrochloride, potassium thiocyanate and bromine analogous to Example 1.

Yield: 56% of theory.
M.p.: 191°–192° C.
Calculated: C-60.92%; H-5.43%; N-13.32%; S-20.33%, Found: C-61.24%; H-5.53%; N-12.97%; S-20.45%.

EXAMPLE 3

2-Amino-7-(4-chlorobenzyl)-6,7,8,9-tetrahydro-5H-thiazolo[4',5':5,4]thieno[2,3-d]azepine dihydrochloride This compound was prepared from 2-amino-6-(4-chlorobenzyl)-5,6,7,8-tetrahydro-4H-thieno[2,3-d]azepine dihydrochloride, potassium thiocyanate and bromine analogous to Example 1.

Yield: 12% of theory.
M.p.: 220° C. (decomposition).
Calculated: C-45.45%; H-4.29%; Cl-25.15%; N-9.94%; S-15.17%, Found: C-45.60%; H-4.15%; Cl-25.10%; N-10.02%; S-15.35%.

EXAMPLE 4

2-Amino-7-propyl-6,7,8,9-tetrahydro-5H-thiazolo[4',5':5,4]thieno[2,3-d]azepine dihydrochloride This compound was prepared from 2-amino-6-propyl-5,6,7,8-tetrahydro-4H-thieno[2,3-d]azepine dihydrochloride, potassium thiocyanate and bromine analogous to Example 1.

Yield: 22% of theory.
M.p.: 230°–233° C. (decomposition).
Calculated: C-42.35%; H-5.63%; Cl-20.83%; N-12.35%; S-18.84%, Found: C-42.25%; H-5.79%; Cl-20.45%; N-12.50%; S-18.95%.

EXAMPLE 5

2-Amino-7-isopropyl-6,7,8,9-tetrahydro-5H-thiazolo[4',5':5,4]thieno[2,3-d]azepine dihydrochloride This compound was prepared from 2-amino-5,6,7,8-tetrahydro-6-isopropyl-4H-thieno[2,3-d]azepine dihydrochloride, potassium thiocyanate and bromine analogous to Example 1.

Yield: 28% of theory.
M.p.: 243°–245° C. (decomposition).
Calculated: C-42.35%; H-5.63%; Cl-20.83%; N-12.35%; S-18.84%, Found: C-42.35%; H-6.00%; Cl-21.00%; N-12.27%; S-18.85%.

EXAMPLE 6

7-Ethyl-2-amino-5,6,7,8-tetrahydro-thiazolo[4',5':5,4]-thieno[3,2-c]pyridine dihydrochloride This compound was prepared from 2-amino-5-ethyl-4,5,6,7-tetrahydro-thieno[3,2-c]pyridine, potassium thiocyanate and bromine analogous to Example 1.

Yield: 24% of theory.
M.p.: >250° C.
Calculated: C-38.46%; H-4.84%; Cl-22.71%; N-13.46%; S-20.53%, Found: C-38.68%; H-4.90%; Cl-22.52%; N-13.41%; S-20.30%.

EXAMPLE 7

2-Amino-7-propyl-5,6,7,8-tetrahydro-thiazolo[4',5':5,4]-thieno[3,2-c]pyridine dihydrochloride This compound was prepared from 2-amino-5-propyl-4,5,6,7-tetrahydro-thieno[3,2-c]pyridine, potassium thiocyanate and bromine analogous to Example 1.

Yield: 29% of theory.
M.p.: 252°–255° C. (decomposition).
Calculated: C-40.49%; H-5.25%; Cl-21.73%; N-12.88%; S-19.65%, Found: C-40.45%; H-5.30%; Cl-21.70%; N-13.02%; S-19.65%.

EXAMPLE 8

2-Amino-7-isopropyl-5,6,7,8-tetrahydro-thiazolo[4',5':5,4]thieno[3,2-c]pyridine dihydrochloride This compound was prepared from 2-amino-5-isopropyl-4,5,6,7-tetrahydro-thieno[3,2-c]pyridine, potassium thiocyanate and bromine analogous to Example 1.

Yield: 23% of theory.
M.p.: 271°–273° C. (decomposition).
Calculated: C-40.49%; H-5.25%; Cl-21.73%; N-12.88%; S-19.65%, Found: C-40.71%; H-5.21%; Cl-21.72%; N-12.91%; S-19.43%.

EXAMPLE 9

7-Allyl-2-amino-5,6,7,8-tetrahydro-thiazolo[4',5':5,4]-thieno[3,2-c]pyridine dihydrochloride This compound was prepared from 5-allyl-2-amino-4,5,6,7-tetrahydro-thieno[3,2-c]pyridine, potassium thiocyanate and bromine analogous to Example 1.

Yield: 22% of theory.
M.p.: 246°–247° C. (decomposition).
Calculated: C-40.74%; H-4.66%; Cl-21.87%; N-12.96%; S-19.77%, Found: C-40.52%; H-4.90%; Cl-21.80%; N-13.06%; S-19.77%.

EXAMPLE 10

Ethyl 2-amino-6,7,8,9-tetrahydro-5H-thiazolo[4',5':5,4]-thieno[2,3-d]azepine-7-carboxylate hydrochloride 7.6 g (0.025 mol) of the sodium salt of 2-amino-6-carbethoxy-5,6,7,8-tetrahydro-4H-thieno[2,3-d]azepine-3-carboxylic acid (prepared by hydrolysis of 7.8 g (0.025 mol) of diethyl 2-amino-5,6,7,8-tetrahydro-4H-thieno[2,3-d]azepine-3,6-carboxylate with aqueous sodium hydroxide) were dissolved in 125 ml of glacial acetic acid, and 7.3 g (0.075 mol) of potassium thiocyanate and 12.5 ml of water were added to the solution. A solution of 4 g (0.025 mol) of bromine in 17 ml of glacial acetic acid was added dropwise to the reaction mixture while stirring, and the resulting mixture was stirred for 3 hours at room temperature. Then, it was poured into 500 ml of water, made alkaline with concentrated aqueous ammonia and extracted five times with chloroform. The combined chloroform extracts were washed three to four times with water, dried with sodium sulfate and potassium carbonate and concentrated by evaporation in vacuo. The solid residue was purified twice by chromatography on a silicagel column (150 ml; chloroform/methanol = 100:3 and chloroform/ethyl acetate = 17:3). After the corresponding fractions had been evaporated in vacuo, the residue was dissolved in a chloroform/methanol mixture (10:1) and acidified with isopropanolic hydrochloric acid. Then, the reaction mixture was again concentrated by evaporation in vacuo, the residue was briefly boiled with ethyl acetate and suction-filtered off after being cooled in ice water.

Yield: 1.7 g (20.4% of theory).
M.p.: 212° C. (decomposition).
Calculated: C-43.17%; H-4.83%; Cl-10.62%; N-12.59%; S-19.21%, Found: C-43.41%; H-5.01%; Cl-10.75%; N-12.79%; S-19.45%.

EXAMPLE 11

2-Amino-6,7,8,9-tetrahydro-5H-thiazolo[4',5':5,4]-thieno[2,3-d]azepine dihydrochloride This compound was prepared from the sodium salt of 2-amino-5,6,7,8-tetrahydro-4H-thieno[2,3-d]azepine-3-carboxylic acid, potassium thiocyanate and bromine analogous to Example 10.

Yield: 22.3% of theory.
M.p. >310° C.
Calculated: C-36.24%; H-4.39%; Cl-23.77%; N-14.09%; S-21.50%, Found: C-36.01%; H-4.58%; Cl-23.60%; N-13.75%; S-21.30%.

EXAMPLE 12

7-Allyl-2-amino-6,7,8,9-tetrahydro-5H-thiazolo[4',5':5,4]thieno[2,3-d]azepine dihydrochloride This compound was prepared from the sodium salt of 6-allyl-2-amino-5,6,7,8-tetrahydro-4H-thieno[2,3-d]azepine-3-carboxylic acid, potassium thiocyanate and bromine analogous to Example 10.

Yield: 15% of theory.
M.p.: 232°–233° C. (decomposition).
Calculated: C-42.60%; H-5.06%; Cl-20.96%; N-12.42%; S-18.95%, Found: C-42.89%; H-4.96%; Cl-20.80%; N-12.78%; S-18.80%.

EXAMPLE 13

2-Amino-5,6,7,8-tetrahydro-6-isopropyl-thiazolo[4',5':5,4]thieno[2,3-c]pyridine dihydrochloride This compound was prepared from the sodium salt of 2-amino-6-isopropyl-4,5,6,7-tetrahydro-thieno[2,3-c]pyridine-3-carboxylic acid, potassium thiocyanate and bromine analogous to Example 10.

Yield: 24.5% of theory.
M.p.: 250° C. (decomposition).
Calculated: C-40.49%; H-5.25%; Cl-21.73%; N-12.88%; S-19.65%, Found: C-40.54%; H-5.26%; Cl-21.80%; N-13.08%; S-19.45%.

EXAMPLE 14

6-Allyl-2-amino-5,6,7,8-tetrahydro-thiazolo[4',5':5,4]-thieno[2,3-c]pyridine dihydrochloride This compound was prepared from the sodium salt of 6-allyl-2-amino-4,5,6,7-tetrahydro-thieno[2,3-c]pyridine-3-carboxylic acid, potassium thiocyanate and bromine analogous to Example 10.

Yield: 7% of theory.
M.p.: 165° C. (decomposition).
Calculated: C-40.74%; H-4.66%; Cl-21.87%; N-12.96%; S-19.77%, Found: C-40.60%; H-4.79%; Cl-21.88%; N-12.96%; S-19.70%.

EXAMPLE 15

6-Ethyl-2-amino-5,6,7,8-tetrahydro-thiazolo[4',5':5,4]-thieno[2,3-c]pyridine dihydrochloride This compound was prepared from the sodium salt of 6-ethyl-2-amino-4,5,6,7-tetrahydro-thieno[2,3-c]pyridine-3-carboxylic acid, potassium thiocyanate and bromine analogous to Example 10.

Yield: 12% of theory.
M.p.: 237° C. (decomposition).
Calculated: C-38.46%; H-4.84%; Cl-22.71%; N-13.46%; S-20.54%, Found: C-38.25%; H-4.84%; Cl-22.40%; N-13.40%; S-20.20%.

EXAMPLE 16

2-Amino-6-propyl-5,6,7,8-tetrahydro-thiazolo[4',5':5,4]-thieno[2,3-c]pyridine dihydrochloride This compound was prepared from the sodium salt of 2-amino-6-propyl-4,5,6,7-tetrahydro-thieno[2,3-c]pyridine-3-carboxylic acid, potassium thiocyanate and bromine analogous to Example 10.

Yield: 12% of theory.
M.p.: 224° C. (decomposition).
Calculated: C-40.49%; H-5.25%; Cl-21.73%; N-12.88%; S-19.65%, Found: C-40.64%; H-5.41%; Cl-21.54%; N-13.28%; S-19.90%.

EXAMPLE 17

2-Amino-6-methyl-5,6,7,8-tetrahydro-thiazolo[4',5':5,4]thieno[2,3-c]pyridine dihydrochloride This compound was prepared from the sodium salt of 2-amino-6-methyl-4,5,6,7-tetrahydro-thieno[2,3-c]pyridine-3-carboxylic acid, potassium thiocyanate and bromine analogous to Example 10.

Yield: 4% of theory.
M.p.: 260°–262° C. (decomposition).
Calculated: C-36.24%; H-4.39%; Cl-23.77%; N-14.09%; S-21.50%, Found: C-36.15%; H-4.37%; Cl-23.65%; N-13.96%; S-21.40%.

EXAMPLE 18

6-Acetyl-2-amino-5,6,7,8-tetrahydro-thiazolo[4',5':5,4]-thieno[2,3-c]hydrochloride This compound was prepared from the sodium salt of 6-acetyl-2-amino-4,5,6,7-tetrahydro-thieno[2,3-c]pyridine-3-carboxylic acid, potassium thiocyanate and bromine analogous to Example 10.

Yield: 5% of theory.
M.p.: 215° C. (decomposition).
Calculated: C-41.44%; H-4.17%; Cl-12.23%; N-14.50%; S-22.13%, Found: C-41.77%; H-3.98%; Cl-12.42%; N-14.50%; S-22.00%.

EXAMPLE 19

2-Amino-7-methyl-5,6,7,8-tetrahydro-thiazolo[4',5':5,4]thieno[3,2-c]pyridine dihydrochloride This compound was prepared from the sodium salt of 2-amino-6-methyl-4,5,6,7-tetrahydro-thieno[3,2-c]pyridine-3-carboxylic acid, potassium thiocyanate and bromine analogous to Example 10.

Yield: 5.4% of theory.

M.p.: 259°-260° C. (decomposition).

Calculated: Molecular ion peak m/e=225, Found: Molecular ion peak m/e=225.

EXAMPLE 20

2-Amino-6,7,8,9-tetrahydro-7-methyl-5H-thiazolo[4',5':5,4]thieno[2,3-d]azepine dihydrochloride 3 g (0.01 mol) of ethyl 2-amino-6,7,8,9-tetrahydro-5H-thiazolo[4',5':5,4]thieno[2,3-d]azepine-7-carboxylate were dissolved in 30 ml of absolute tetrahydrofuran, and the solution was slowly added dropwise at room temperature, while stirring, to a suspension of 3 g (0.08 mol) of lithium aluminum hydride in 50 ml of absolute tetrahydrofuran. The temperature of the reaction mixture was kept below 30° C. by occasional cooling in ice water. The mixture was then stirred for 6 hours at room temperature and allowed to stand overnight. The next day, 18 ml of ethyl acetate were slowly added, while cooling with ice, so that the temperature was kept below 25° C. Finally, 10 ml of water and 3 ml of aqueous 10% sodium hydroxide were carefully added. The hydroxide precipitate was suction-filtered on diatomaceous earth and washed several times with a hot mixture of chloroform and methanol or with chloroform. After the filtrate had been evaporated, 3 g of a viscous dark oil remained, which was purified by column chromatography on silica gel (chloroform/methanol/concentrated aqueous ammonia=8.5:1.5:0.15). After the corresponding fractions had been evaporated, the residue was dissolved in isopropanol, and the solution was acidified with isopropanolic hydrochloric acid. The precipitate dihydrochloride was suction-filtered off and washed with cold isopropanol.

Yield: 0.55 g (18% of theory).

M.p.: 271°-273° C. (decomposition).

Calculated: C-38.46%; H-4.84%; Cl-22.71%; N-13.46%; S-20.53%, Found: C-38.80%; H-4.50%; Cl-22.90%; N-13.37%; S-20.55%.

EXAMPLE 21

2-Amino-6,7,8,9-tetrahydro-6-methyl-5H-thiazolo[4',5':5,4]thieno[2,3-c]azepine dihydrochloride This compound was prepared by reduction of 2-amino-6-carbethoxy-6,7,8,9-tetrahydro-5H-thiazolo[4',5':5,4]thieno[2,3-c]azepine with lithium aluminum hydride analogous to Example 20.

Yield: 26% of theory.

M.p.: 217°-220° C. (decomposition).

Calculated: C-38.46%; H-4.84%; Cl-22.71%; N-13.46%; S-20.53%, Found: C-38.25%; H-4.99%; Cl-22.50%; N-13.54%; S-20.25%.

EXAMPLE 22

6-Ethyl-2-amino-5,6,7,8-tetrahydro-thiazolo[4',5':5,4]-thieno[2,3-c]pyridine dihydrochloride This compound was prepared by reduction of 6-acetyl-2-amino-5,6,7,8-tetrahydro-thiazolo[4',5':5,4]-thieno[2,3-c]pyridine with lithium aluminum hydride analogous to Example 20.

Yield: 29% of theory.

M.p.: 237° C. (decomposition).

Calculated: Molecular ion peak m/e=239, Found: Molecular ion peak m/e=239.

EXAMPLE 23

8-Ethyl-2-amino-6,7,8,9-tetrahydro-5H-thiazolo[4',5':5,4]thieno[3,2-c]azepine dihydrochloride This compound was prepared from 5-ethyl-2-amino-5,6,7,8-tetrahydro-4H-thieno[3,2-c]azepine dihydrobromide, potassium thiocyanate and bromine analogous to Example 1.

Yield: 21% of theory.

M.p.: 241°-242° C. (decomposition).

Calculated: C-40.49%; H-5.25%; Cl-21.73%; N-12.88%; S-19.65%, Found: C-40.97%; H-5.34%; Cl-22.05%; N-13.07%; S-20.15%.

EXAMPLE 24

2-Amino-7-(2-chlorobenzyl)-6,7,8,9-tetrahydro-5H-thiazolo[4',5':5,4]thieno[2,3-d]azepine dihydrochloride This compound was prepared from 2-amino-6-(2-chlorobenzyl)-5,6,7,8-tetrahydro-4H-thieno[2,3-d]azepine dihydrochloride, potassium thiocyanate and bromine or copper sulfate as oxidizing agent analogous to Example 1.

Yield: 18% of theory.

M.p.: 203°-206° C. (decomposition).

Calculated: C-45.45%; H-4.29%; N-9.94%; S-15.17%, Found: C-45.21%; H-4.17%; N-9.83%; S-15.15%.

EXAMPLE 25

2-Amino-7-propionyl-6,7,8,9-tetrahydro-5H-thiazolo[4',5':5,4]thieno[2,3-d]azepine This compound was prepared from 2-amino-6-propionyl-5,6,7,8-tetrahydro-4H-thieno[2,3-d]azepine hydrochloride, potassium thiocyanate and bromine analogous to Example 1.

Yield: 25% of theory.

M.p.: 222° C.

Calculated: C-51.22%; H-5.37%; N-14.93%; S-22.79%, Found: C-51.25%; H-5.44%; N-15.02%; S-22.66%.

The compounds of the present invention, that is, those embraced by formula I and their non-toxic, pharmacologically acceptable acid addition salts, have useful pharmacodynamic properties. More particularly, they exhibit very effective bradycardiac activity and have a favorable effect on the blood pressure in warm-blooded animals such as rats.

The above pharmacological properties were ascertained by the standard test methods described below, and the results of these tests for a few representative species of the genus are shown in the table, where A = 7-ethyl-2-amino-6,7,8,9-tetrahydro-5H-thiazolo[4',5':5,4]thieno[2,3-d]azepine dihydrochloride, B = 2-amino-7-benzyl-6,7,8,9-tetrahydro-5H-thiazolo[4',5':5,4]thieno[2,3d]azepine, C = 7-allyl-2-amino-6,7,8,9-tetrahydro-5H-thiazolo[4',5':5,4]thieno[2,3-d]azepine dihydrochloride, D = 2-amino-6,7,8,9-tetrahydro-7-isopropyl-5H-thiazolo[4',5':5,4]thieno[2,3-d]azepine dihydrochloride, E = 6-ethyl-2-amino-5,6,7,8-tetrahydro-thiazolo[4',5':5,4]thieno[2,3c]pyridine dihydrochloride, F = 2-amino-5,6,7,8-tetrahydro-6-propyl-thiazolo[4',5':5,4]thieno[2,3-c]pyridine dihydrochloride, G = 2-amino-5,6,7,8-tetrahydro-6-methyl-thiazolo[4',5':5,4]thieno[2,3-c]pyridine dihydrochloride, and H = 2-amino-5,6,7,8-tetrahydro-5H-thiazolo[4',5':5,4]thieno[2,3-d]azepine dihydrochloride.

1. Effect on blood pressure and heart rate

Method:

Changes in circulation after intravenous injection of the test substance were recorded in the intact anesthetized rat.

Male rats weighing 200 g were anesthetized with pentobarbital (50 mg/kg i.p.). The animals breathed spontaneously through a tracheal cannula secured in position. The blood pressure was measured at an A. carotis using an electromechanical pressure transducer; the pulse wave triggered a tachograph which recorded the heart rate continuously. Both parameters were recorded on the polygraph. The test substance was injected into a V. jugularis through a catheter.

The test substances, when administered at a dosage of 3 mg/kg i.v., produced a brief initial increase in blood pressure followed by a longer-lasting reduction in pressure. The heart rate was markedly lowered for a long period. The maximum values are given in the table which follows:

TABLE I

| Compound | Dosage mg/kg i.v. | Blood pressure in mm Hg pressor phase | Blood pressure in mm Hg depressor phase | Lowering of heart rate beats/minute |
|---|---|---|---|---|
| A | 3 | +52 | −18 | −90 |
| B | 3 |  | −25 | −95 |
| C | 3 | +17 | −15 | −150 |
| D | 3 | +23 | −20 | −78 |
| E | 3 | +30 | −29 | −108 |
| F | 3 | +16 | −12 | −65 |
| G | 3 | +46 | −30 | −95 |
| H | 1.5 | +38 | −34 | −100 |

2. Effect on presynaptic α-adrenoceptors: Inhibition of electrically triggered tachycardia Method:

At the adrenergic nerve ending there is an autoregulating system for the relase of noradrenaline. The stimulation of presynaptic α-adrenoreceptors has an inhibiting effect on the release of noradrenaline and thus restricts adrenergic neurotransmission. Accordingly, if these "feedback receptors" are stimulated, the effect of a given adrenergic stimulation on the responding organ can be attenuated. In the electrically stimulated spinal rat, the tachycardia induced electrically in the heart is attenuated by substances with a presynaptic α-mimetic activity.

Description of the test:

Male rats weighing from 350 to 400 g were anesthetized with pentobarbital (50 mg/kg i.p.), vagotomized, treated with atropine (1 mg/kg s.c.) and fitted with a tracheal cannula. After enucleation of one eye, the orbits were pierced, the brain was destroyed, and a metal rod was pushed through the vertebral canal. The animals were artificially ventilated and pre-treated with gallamine (4 mg/kg i.v.). The metal rod used was 2.5 mm in diameter and was insulated (stove-enamelled). The rod was bare metal from the 7th to 8th centimeter from the tip. This exposed part came to rest at the level of the last cervical vertebra and first thoracic vertebra when the rod was inserted. Supermaximum stimulation was effected by means of a stimulator against a counter-electrode inserted in the skin of the animal's neck (square-wave pulses 50 V, 2 ms; 0.2 Hz; duration of stimulation 25 s).

The blood pressure was measured at an A. carotis by means of an electromechanical pressure transducer. The pulse wave triggered a tachograph which continuously recorded the heart rate. Both signals were recorded on a multi-channel recorder.

The dosage ($D_{50}$) which inhibits electrically induced tachycardia by 50% was determined.

TABLE II

| Compound | Inhibition of electrically induced tachycardia $D_{50}$ |
|---|---|
| A | 290 μg/kg i.v. |

3. Effect on postsynaptic α-adrenoceptors: Increase in blood pressure in the spinal rat Method:

The increase in blood pressure occurring after the stimulation of postsynaptic α-adrenoreceptors is measured in the spinal rat.

Description of test:

Male rats weighing from 200 to 250 g were anesthetized (1.2 g/kg of urethane i.p., 1 mg/kg of atropine s.c.). Then the central canal of the spinal cord was opened up. The spinal cord was severed at $C_1$, and the medulla oblongata and the brain were destroyed with a metal probe. The animals were artificially ventilated; a polyethylene catheter was secured in a jugular vein, and the blood pressure was recorded from an A. carotis by means of a Statham element on a Grass polygraph.

The dosage ($D_{30}$) which increased the arterial blood pressure by 30 mmHg was determined.

TABLE III

| Compound | Blood pressure-increasing activity $D_{30}$ |
|---|---|
| A | 145 μg/kg i.v. |
| H | 0.36 mg/kg i.v. |

4. Acute toxicity:

The acute toxicity was determined in mice after oral or intravenous administration (observation period: 14 days):

TABLE IV

| Compound | $LD_{50}$ | |
|---|---|---|
| A | 34 mg/kg i.v. | 320 mg/kg p.o. |
| F |  | >300 mg/kg p.o. |

On the basis of their pharmacological properties the novel compounds of the formula I and their non-toxic pharmacologically acceptable acid addition salts are useful for treating cardiac and circulatory disorders, anginal complaints and for lowering the heart rate.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.02 to 0.15 mg/kg body weight, preferably 0.02 to 0.08 mg/kg body weight, 1 to 3 times daily.

The following examples illustrate a few pharmaceutical compositions comprising a compound of the present invention as an active ingredient and represent the best modes contemplated of using the invention. The parts are parts by weight unless otherwise specified.

EXAMPLE 26

Coated tablets
The tablet core composition is compounded from the following ingredients:

| | |
|---|---|
| 7-Ethyl-2-amino-6,7,8,9-tetrahydro-5H—thiazolo[4',5':5,4]-thieno-[2,3-d]azepine dihydrochloride | 5.0 parts |
| Lactose | 33.5 parts |
| Corn starch | 10.0 parts |
| Gelatin | 1.0 parts |
| Magnesium stearate | 0.5 parts |
| Total | 50.0 parts |

Preparation:
A mixture of the active ingredient, the lactose and the corn starch is granulated through a 1 mm-mesh screen with an aqueous 10% gelatin solution, then dried at 40° C. and again passed through this screen. The granulate thus obtained is mixed with the magnesium stearate and compressed into 50 mg-tablet cores. The composition must be prepared in a darkened room.

The tablet cores thus produced are coated in the usual way with a thin shell consisting essentially of sugar and talcum. The finished coated tablets are polished with beeswax. Each tablet contains 5 mg of the active ingredient.

EXAMPLE 27

Drop solution
The solution is compounded from the following ingredients:

| | |
|---|---|
| Methyl p-hydroxybenzoate | 0.035 parts |
| Propyl p-hydroxybenzoate | 0.015 parts |
| Anisole | 0.05 parts |
| Menthol | 0.06 parts |
| Ethanol, pure | 10.0 parts |
| 7-Ethyl-2-amino-6,7,8,9-tetrahydro-5H—thiazolo-[4',5':5,4]-thieno[2,3-d]azepine dihydrochloride | 0.5 parts |
| Citric acid | 0.7 parts |
| Secondary sodium phosphate.2H$_2$O | 0.3 parts |
| Sodium cyclamate | 1.0 parts |
| Glycerol | 15.0 parts |
| Distilled water q.s.ad | 100.0 parts by vol. |

Preparation:

The p-hydroxybenzoates, the anisole and the menthol are dissolved in the ethanol (solution I).

The buffer substances, the active ingredient and the sodium cyclamate are dissolved in a sufficient amount of distilled water, and the glycerol is added (solution II). Solution I is stirred into solution II, and the mixture is diluted to the indicated volume with distilled water. The finished solution is filtered through a suitable filter and filled into brown 100 ml-bottled equipped with a dropping spout. 1 ml (about 20 drops) contains 5 mg of the active ingredient. The solution must be prepared and bottled under exclusion of light and in an insert gas atmosphere.

EXAMPLE 28

Suppositories
The suppository composition is compounded from the following ingredients:

| | |
|---|---|
| 7-Ethyl-2-amino-6,7,8,9-tetrahydro-5H—thiazolo[4',5':5,4]thieno-[2,3-d]azepine dihydrochloride | 10.0 parts |
| Suppository base (e.g. cocoa butter) | 1690.0 parts |
| Total | 1700.0 parts |

Preparation:
The finely powdered active ingredient is stirred into the molten suppository base which has been cooled to 40° C., using an immersion homogenizer. At 35° C., 1.7 gm-portions of the composition are poured into slightly chilled suppository molds and allowed to harden therein. Each suppository contains 10 mg of the active ingredient.

EXAMPLE 29

Hypodermic solution
The solution is compounded from the following ingredients:

| | |
|---|---|
| 7-Ethyl-2-amino-6,7,8,9-tetrahydro-5H—thiazolo[4',5':5,4]thieno-[2,3-d]azepine dihydrochloride | 5.0 parts |
| Citric acid | 7.0 parts |
| Secondary sodium phosphate.H$_2$O | 3.0 parts |
| Sodium pyrosulfite | 1.0 parts |
| Distilled water q.s.ad | 1000.0 parts by vol |

Preparation:
The buffers, the active ingredient and the sodium pyrosulfite are successively dissolved in distilled water which has been cooled under a current of $CO_2$. The solution is diluted to the indicated volume with distilled water and filtered to remove any pyrogens.

Bottling: in brown 1 cc-ampules under protective gas.
Sterilization: 20 minutes at 120° C.
The hypodermic solution must be prepared and bottled in a darkened room.

Any one of the other compounds embraced by formula I or a non-toxic, pharmacologically acceptable acid addition salt thereof may be substituted for the particular active ingredient in Examples 25 through 28. Likewise, the amount of active ingredient in these illustrative examples may be varied to achieve the dosage unit range set forth above, and the amounts and nature of the inert pharmaceutical carrier may be varied to meet particular requirements.

We claim:
1. A compound of the formula

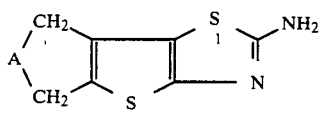

wherein A is

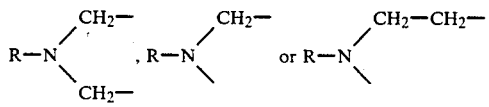

and

R is hydrogen, alkyl of 1 to 5 carbon atoms, alkanoyl of 1 to 5 carbon atoms, alkenyl of 3 to 5 carbon atoms, (alkoxy of 1 to 4 carbon atoms) carbonyl, or aralkyl of 7 to 11 carbon atoms optionally halo-substituted;

or a non-toxic, pharmacologically acceptable acid addition salt thereof.

2. A 2-amino-6,7,8,9-tetrahydro-5H-thiazolo[4',5':5,4]thieno[2,3d]azepine, 2-amino-5,6,7,8-tetrahydro-thiazolo[4',5':5,4]thieno[3,2c]pyridine, 2-amino-5,6,7,8-tetrahydro-thiazolo[4',5':5,4]thieno[2,3-c]pyridine or 2-amino-6,7,8,9-tetrahydro-5H-thiazolo[4',5':5,4]thieno[2,3-c]azepine derivative of claim 1, where
R is hydrogen, alkyl of 1 to 4 carbon atoms, alkanoyl of 1 to 3 carbon atoms, (alkoxy of 1 to 3 carbon atoms)carbonyl, benzyl, chlorobenzyl, bromobenzyl or allyl, or a non-toxic, pharmacologically acceptable acid addition salt thereof.

3. A 2-amino-6,7,8,9-tetrahydro-5H-thiazolo[4',5':5,4]thieno[2,3-d]azepine or 2-amino-5,6,7,8-tetrahydro-thiazolo[4',5'-5,4]thieno[2,3-c]pyridine derivative of claim 1, where
R is hydrogen, alkyl of 1 to 3 carbon atoms, allyl or benzyl, or a non-toxic, pharmacologically acceptable acid addition salt thereof.

4. A 2-amino-6,7,8,9-tetrahydro-5H-thiazolo[4',5':5,4]thieno[2,3-d]azepine derivative of claim 3 or a non-toxic, pharmacologically acceptable acid addition salt thereof.

5. A 2-amino-5,6,7,8-tetrahydro-thiazolo[4',5':5,4]-thieno[2,3-c]pyridine derivative of claim 3 or a non-toxic, pharmacologically acceptable acid addition salt thereof.

6. A compound of claim 4 which is 7-ethyl-2-amino-6,7,8,9-tetrahydro-5H-thiazolo[4',5':5,4]thieno[2,3-d]azepine or a non-toxic, pharmacologically acceptable acid addition salt thereof.

7. A bradycardiac pharmaceutical composition consisting essentially of an inert pharmaceutical carrier and an effective bradycardiac amount of a compound of claim 1.

8. The method of lowering the heart rate of a warm-blooded animal in need thereof, which comprises perorally, parenterally or rectally administering to said animal an effective bradycardiac amount of a compound of claim 1.

* * * * *

UNITED STATES PATENT AND TRADEMARK OFFICE
CERTIFICATE OF CORRECTION

PATENT NO. : 4,575,504
DATED : March 11, 1986
INVENTOR(S) : ROBERT SAUTER ET AL.

It is certified that error appears in the above-identified patent and that said Letters Patent is hereby corrected as shown below:

Col. 3, lines 1-5: [chemical structures showing "R—N with CH$_2$ branches"]

should read: [corrected chemical structures showing R$_1$—N with CH$_2$ branches]

Col. 7, line 2: "filrates" should read -- filtrates --.

Col. 13, line 5: "[2,3c]" should read -- [2,3-c] --.

Col. 17, line 34: "[3,2c]" should read -- [3,2-c] --.

Signed and Sealed this

Twenty-second Day of July 1986

[SEAL]

Attest:

DONALD J. QUIGG

Attesting Officer    Commissioner of Patents and Trademarks